United States Patent [19]

Ciceri et al.

[11] Patent Number: 5,491,154

[45] Date of Patent: Feb. 13, 1996

[54] PHARMACEUTICAL PREPARATION FOR THE ORAL ADMINISTRATION OF DIHYDROPYRIDINES

[75] Inventors: Silvana Ciceri, Como; Gilberto Dondi, Cusano Milanino; Paolo Scurati, Milan, all of Italy

[73] Assignee: Bayer S.P.A., Milan, Italy

[21] Appl. No.: 99,288

[22] Filed: Jul. 29, 1993

[30] Foreign Application Priority Data

Aug. 5, 1992 [IT] Italy ................... MI92A1930

[51] Int. Cl.⁶ .................. A61K 31/44; C07D 211/90; C07D 213/55
[52] U.S. Cl. ............................. 514/356; 546/321
[58] Field of Search .................. 514/356; 546/321

[56] References Cited

U.S. PATENT DOCUMENTS 3,485,847  12/1969  Bossert et al. .................. 546/321
4,154,839  5/1979  Wehinger et al. ................ 514/356
4,406,906  9/1983  Meyer et al. ..................... 514/356

FOREIGN PATENT DOCUMENTS 1247      4/1979   European Pat. Off. .......... 514/356
410422    1/1991   European Pat. Off. .......... 514/356
487335    5/1992   European Pat. Off. .......... 514/356
2081361  12/1971   France .............................. 514/356

OTHER PUBLICATIONS

Chem. Abstracts. vol. 98 (8) 98:59913(b), Feb. 21, 1983.

*Primary Examiner*—Alan L. Rotman
*Attorney, Agent, or Firm*—Sprung Horn Kramer & Woods

[57] ABSTRACT

Pharmaceutical preparations for the oral administration of dihydropyridines in beverage form are described.

These preparations are characterized in that they contain a coprecipitate of essentially amorphous dihydropyridine with a suitable pharmacologically acceptable polymer. The corresponding preparation processes are also described.

1 Claim, 3 Drawing Sheets

Fig. 5

| Test | T = 0 | 25°C | 30°C | 40°C |
|---|---|---|---|---|
| Appearance | unchanged | unchanged | unchanged | unchanged |
| pH | 5,26 | 5,29 | 5,42 | 5,38 |
| Solution test after 30' | 80,5% | 78,55% | 81,5% | 85,2% |
| Degradation products | not measurable | not measurable | not measurable | 0,43% |
| Content mg/individual dose | 30,8 | 30,5 | 30,6 | 30,4 |

Fig. 6

| Test | T = 0 | 25°C | 30°C | 40°C |
|---|---|---|---|---|
| Appearance | unchanged | unchanged | unchanged | unchanged |
| pH | 5,33 | 5,32 | 5,29 | 5,30 |
| Solution test after 30' | 81,2% | 75,6% | 76,8% | 82,7% |
| Degradation products | not measurable | not measurable | not measurable | 0,30% |
| Content mg/individual dose | 30,3 | 30,9 | 30,7 | 30,3 |

PHARMACEUTICAL PREPARATION FOR THE ORAL ADMINISTRATION OF DIHYDROPYRIDINES

The administration of pharmaceutical preparations based on dihydropyridines is a quite awkward problem, because of the extremely low solubility of these chemical compounds.

The method usually used to obtain an adequate bioavailability is based on the administration of these dihydropyridines in amorphous or micellar form, among which nimodipine, nifedipine and nisoldipine are the best-known representatives.

The amorphous state is customarily obtained by preparations of coprecipitates with pharmacologically acceptable polymers, such as polyvinylpyrrolidone (PVP), while the formation of micelles is customarily obtained by dilution of solutions which have high contents of surfactants and contain alcohols as auxiliaries.

The common problem in both cases is how the crystal formation processes can be prevented, since they can therefore dramatically affect the bioavailability of some dihydropyridines, among them nimodipine, since the solubility of the amorphous and crystalline form varies greatly.

Among the various available pharmaceutical forms of nimodipine, the drop preparation has remarkable and valuable advantages with respect to the taking of this preparation, which is used for the treatment of an inadequate cerebral circulation, on the part of elderly patients, who are the main group of possible patients.

A weak point of the pharmaceutical drop preparation is the necessity that the patient must measure out (i.e. count) the drops himself. This apparently simple activity can actually be a not inconsiderable obstacle for an elderly patient and can be perceived as very arduous.

Among the various possible solutions, that which has shown itself to be the most suitable is the one which consists of the preparation of a water-dispersible individual dose, which is adjusted organoleptically such that the unpleasant taste of the active ingredient is masked. Orange juice granules and the appropriate flavouring have proven very expedient for this. The presence of an effervescent system also contributes to the acceptability of the preparation and to the safe dispersion of the active ingredient.

In order that the dissolution of the dihydropyridine, e.g. nimodipine is ensured, the nimodipine/PVP coprecipitate was employed in the formulation, the amount of PVP being proportioned such that it is adequate for the safe retention of the amorphous state of the nimodipine without causing an undesired formation of foam during the effervescent activity.

The dihydropyridine/PVP especially the nimodipine/PVP coprecipitate can be prepared by various procedures, which are illustrated, by way of example, in the following.

Dissolution of nimodipine (1 part) and PVP (3 parts) in organic solvent, e.g. acetone (3 parts), with subsequent drying in an oven under reduced pressure.

Atomisation of a solution of nimodipine and PVP in organic solvent.

Dissolution of nimodipine (1 part) and PVP 25 (3 parts) in tetrahydrofuran (3 pars). Precipitation by means of petroleumbenzine (7 parts). Filtration and drying of the coprecipitate.

Drying of a solution of nimodipine and PVP in organic solvent in a fluidised bed apparatus under reduced pressure.

Freeze-drying of a solution of nimodipine and PVP in a suitable organic solvent, such as tert-butyl alcohol, etc.

The optimum nimodipine/PVP ratio was determined by investigation of the solution profile of an amount of coprecipitate equivalent to 15 mg of nimodipine, in the equipment known from the various pharmacopoeias and suitable for this.

| Medium volume | 1300 ml of 0.1N HCl |
|---|---|
| T° = 37° C. | |
| Speed of the stirrer blade: | 50 rpm. |

The results obtained with the nimodipine/PVP 25 coprecipitate are represented in FIG. 1. They confirm that there is a direct dependence of the amount of active ingredient which is released on the amount of PVP which is present in the coprecipitate. If the ratio 1:3 was used, a very satisfactory dissolution profile was obtained, an 80% dissolution being achieved after 15 minutes, which proved virtually stable for more than 2 hours.

The abovementioned values point to a supersaturation with a small, or even no, tendency for recrystallisation. Higher amounts of PVP are therefore superfluous from this point of view, while they could lead to an undesired superfluous formation of foam. According to the present invention, other types of PVP, such as e.g. PVP 30 and PVP 90, can also be employed.

In comparison to PvP 25, the results in FIG. 2 show that with the ratio nimodipine:PVP 30=1:2 higher concentrations are obtained and with the ratio 1:3, on the other hand, no difference exists.

The coprecipitate obtained with PVP 90 is a third example. In this case, only coprecipitates with the ratio 1:1 or 1:2 were prepared, because with the ratio 1:3 an unusable plastic mass is obtained.

Using PVP 90, with the ratio 1:1 a good profile is obtained which appears to be unchangeable with the ratio 1:2.

The preferred polyvinylpyrrolidole according to the present invention is PVP 25; the preferred nimodipine:PVP ratio is 1:3.

As far as orange juice granules are concerned, they can be prepared with various concentrations by means of a fluidised bed granulator by spraying orange juice concentrate onto very fine sucrose. The effervescent substance pair was adjusted such that the finished beverage had a pH between 5 and 6, which is an optimum range for the retention of a pleasant taste with such preparations.

In the following, the invention is illustrated by some exemplary preparations based on pharmaceutically active dihydropyridines in effervescent granule form. In the examples, the parts are shown as parts by weight and the ratios as weight/weight data.

BRIEF DESCRIPTION OF THE DRAWINGS

FIG. 5 lists the properties relating to stability of the composition of Example 2.

FIG. 6 lists the properties relating to stability of the composition of Example 3.

EXAMPLE 1

Figure 1:
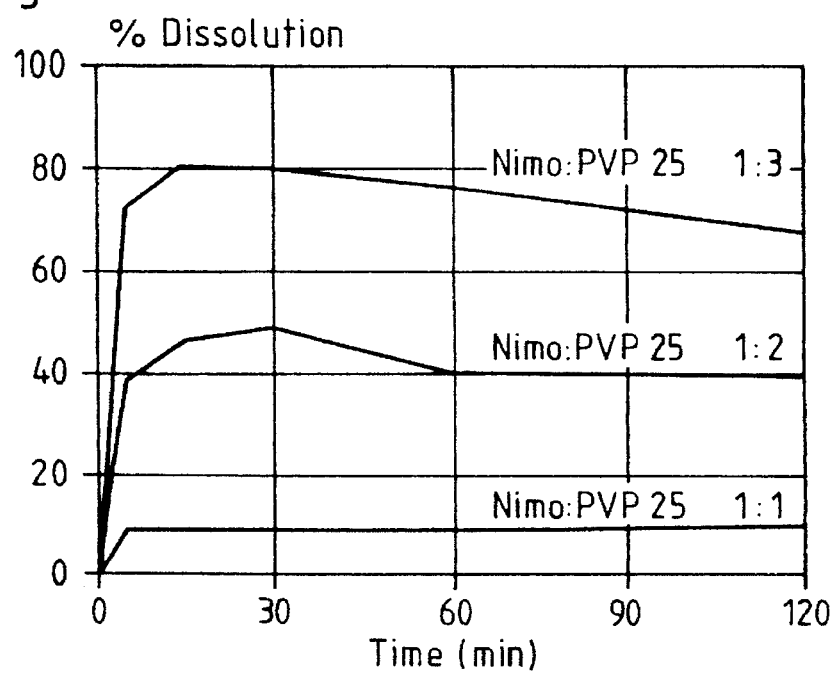
FIG. 1 depicts the dissolution profile of the nimodipine/PVP 25 precipitate at different ratios.
Figure 2:
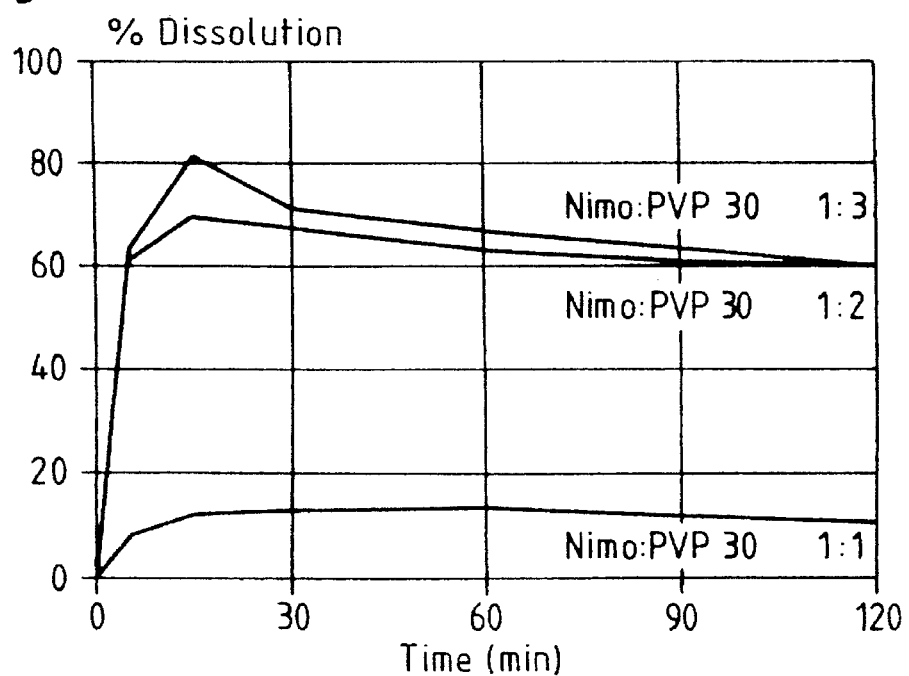
FIG. 2 depicts the dissolution profile of the nimodipine/PVP 30 precipitate at different ratios.
Figure 3:
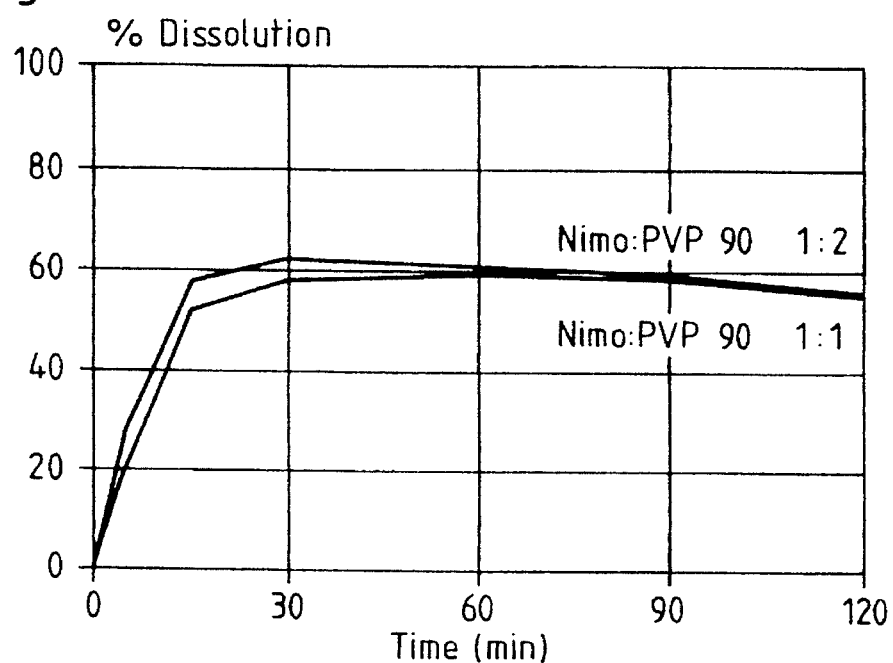
FIG. 3 depicts the dissolution profile of the nimodipine/PVP 90 precipitate at different ratios.
Figure 4:
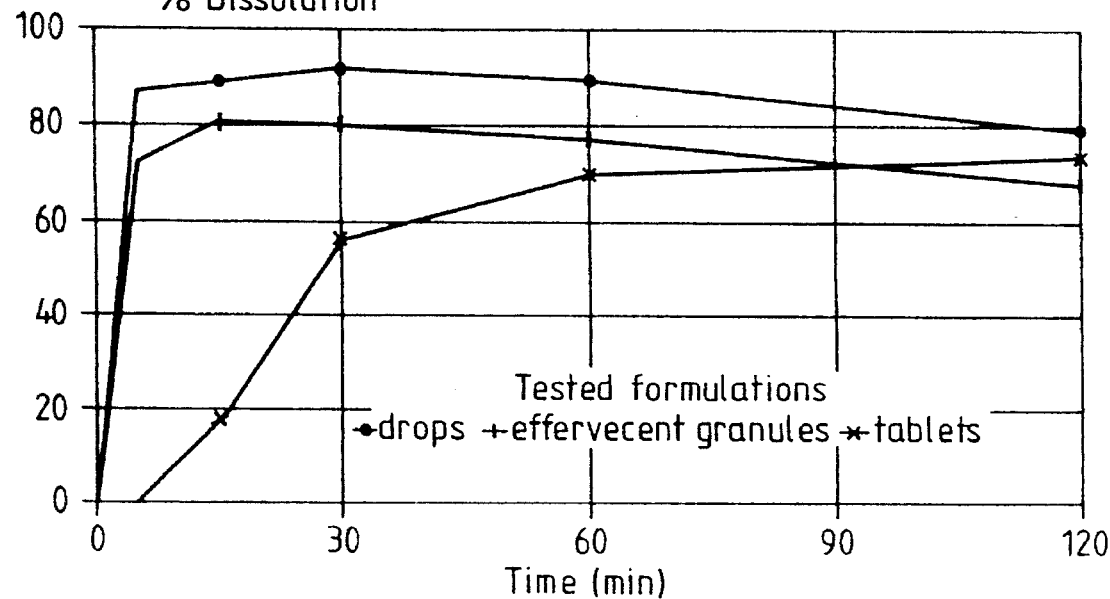
FIG. 4 depicts the dissolution profile of the tested formulations.

| | |
|---|---|
| Coprecipitate of nimodipine:PVP 25 (1:3) | 120.0 mg |
| Citric acid | 800.0 mg |
| Na bicarbonate | 800.0 mg |
| Citrus flavouring | 50.0 mg |
| Orange granules* q.s. to | 3.5 g |
| *Exemplary composition of the orange granules: | |
| Sucrose | 1500.0 mg |
| Orange juice (dry) | 200.0 mg |
| Saccharin sodium | 7.0 mg |
| E 110 | 1.0 mg |

Nimodipine and PVP 25 are dissolved in the ratio 1:3 in acetone (4 parts) at room temperature; the mixture is stirred until it is completely dissolved; after removal of the acetone by evaporation, the coprecipitate is obtained in the form of an amorphous brittle solid, which is then granulated and mixed with the other constituents.

EXAMPLE 2

| | |
|---|---|
| Coprecipitate of nimodipine:PVP 30 (1:2) | 90.0 mg |
| Citric acid | 800.0 mg |
| Na bicarbonate | 800.0 mg |
| Citrus flavouring | 50.0 mg |
| Orange granules* (see above) q.s. to | 4.0 g |

The procedure is as in Example 1.

EXAMPLE 3

| | |
|---|---|
| Coprecipitate of nifedipine:PVP 25 (1:3) | 40.0 mg |
| Citric acid | 800.0 mg |
| Na bicarbonate | 800.0 mg |
| Citrus flavouring | 50.0 mg |
| Orange granules* (see above) q.s. to | 4.0 g |

The procedure is as in Example 1.

EXAMPLE 4

| | |
|---|---|
| Coprecipitate of nisoldipine:PVP 25 (1:3) | 40.0 mg |
| Citric acid | 800.0 mg |
| Na bicarbonate | 800.0 mg |
| Citrus flavouring | 50.0 mg |
| Orange granules* (see above) q.s. to | 3.5 g |

The procedure is as in Example 1.

The results, which relate to the stability of the abovementioned preparations, are represented in FIGS. 5 and 6.

EXAMPLE 5

| | |
|---|---|
| Coprecipitate from nimodipine:PVP 25 (1:3) | 120.0 mg |
| Citrus flavouring | 50.0 mg |
| Lemon granules* (as above) p.s. to | 5.0 g |

The procedure is as in Example 1.

EXAMPLE 6

Preparation of a coprecipitate by means of a fluidised bed granulator under reduced pressure.

Nimodipine (1 part) and PVP 25 (3 parts) are dissolved in acetone (8 parts) at room temperature; the mixture is stirred until it is completely dissolved; the solution is then spray-dried under the following conditions in a fluidised bed apparatus under reduced pressure with recovery of the solvent:

| | |
|---|---|
| Inlet temperature | 120°–150° C. |
| Outlet temperature | 50°–80° C. |
| Spray throughput | 1–1.5 kg/min |

EXAMPLE 7

Preparation of a coprecipitate by freeze-drying.

Nimodipine (5 parts) and PVP 25 (15 parts) are dissolved in tert-butyl alcohol (80 parts). The batch is then frozen at −10° C. to −20° C. and lyophilised according to customary processes.

Primary drying: gradual warming to +20° C.

Secondary drying: 4–5 hours at +40° C.

EXAMPLE 8

| | |
|---|---|
| Coprecipitate of nimodipine:poloxamer F 127 (1:3) | 120.0 mg |
| E 110 | 1.0 mg |
| Saccharin | 7.0 mg |
| Citrus flavouring | 50.0 mg |
| Sucrose q.s. to | 3.5 g |

The nimodipine/poloxamer F 127 (1:3) coprecipitate is dissolved in acetone (5 parts); the solution obtained in this way is employed for the granulation of very fine sucrose (22.5 parts). The mixture is screened and dried under reduced pressure.

The residue is granulated and mixed with further sucrose and citrus flavouring.

We claim:

1. A pharmaceutical composition which consists essentially of

| | | |
|---|---|---|
| Coprecipitate of nimodipine:PVP 25 (1:3) | | 120.0 mg |
| Citric acid | | 800.0 mg |
| Na bicarbonate | | 800.0 mg |
| Citrus Flavouring | | 50.0 mg |
| Orange granules | q.s. to | 3.5 g |

* * * * *